United States Patent
Rebbeor et al.

(10) Patent No.: US 12,144,849 B2
(45) Date of Patent: Nov. 19, 2024

(54) COMPOSITION COMPRISING HIGHLY-CONCENTRATED ALPHA1 PROTEINASE INHIBITOR AND METHOD FOR OBTAINING THEREOF

(71) Applicant: GRIFOLS WORLDWIDE OPERATIONS LIMITED, Dublin (DE)

(72) Inventors: James Rebbeor, Garner, NC (US); Charles Miller, Apex, NC (US); Anthony Klos, Raleigh, NC (US); Eric Allgaier, Wake Forest, NC (US); Thomas P. Zimmerman, Raleigh, NC (US); Kevin Wee, Wake Forest, NC (US); Michelle StPeter, Graner, NC (US); Kelly Glancy, Holly Springs, NC (US)

(73) Assignee: GRIFOLS WORLDWIDE OPERATIONS LIMITED, Dublin (IE)

( * ) Notice: Subject to any disclaimer, the term of this patent is extended or adjusted under 35 U.S.C. 154(b) by 0 days.

(21) Appl. No.: 18/316,850

(22) Filed: May 12, 2023

(65) Prior Publication Data

US 2023/0277636 A1    Sep. 7, 2023

Related U.S. Application Data

(63) Continuation of application No. 17/448,509, filed on Sep. 22, 2021, now Pat. No. 11,701,412, which is a continuation of application No. 16/529,686, filed on Aug. 1, 2019, now Pat. No. 11,253,578.

(60) Provisional application No. 62/713,673, filed on Aug. 2, 2018.

(51) Int. Cl.
| | | |
|---|---|---|
| A61K 38/55 | (2006.01) | |
| A61K 47/12 | (2006.01) | |
| A61K 47/26 | (2006.01) | |
| A61K 47/30 | (2006.01) | |

(52) U.S. Cl.
CPC .............. *A61K 38/55* (2013.01); *A61K 47/12* (2013.01); *A61K 47/26* (2013.01); *A61K 47/30* (2013.01)

(58) Field of Classification Search
CPC ........ A61K 38/55; A61K 47/12; A61K 47/26; A61K 47/30; A61K 47/183; A61K 38/57; A61K 9/08; A61K 9/0073; A61K 9/0019; A61K 45/00; A61P 11/00; A61P 1/16
See application file for complete search history.

(56) References Cited

U.S. PATENT DOCUMENTS

| | | |
|---|---|---|
| 5,981,715 A | 11/1999 | Hwang et al. |
| 6,462,180 B1 | 10/2002 | Lebing et al. |
| 7,879,800 B2 | 2/2011 | Bauer |
| 8,124,736 B2 | 2/2012 | Kee et al. |
| 8,728,315 B2 | 5/2014 | de los Reyes et al. |
| 9,616,126 B2 | 4/2017 | Guo et al. |
| 2008/0312136 A1 | 12/2008 | Durrani et al. |
| 2011/0002909 A1 | 1/2011 | Arora et al. |
| 2011/0237781 A1 | 9/2011 | Lebing et al. |
| 2014/0206753 A1 | 7/2014 | Guild et al. |
| 2015/0133636 A1 | 5/2015 | Xenopoulos et al. |
| 2017/0312282 A1 | 11/2017 | Robinson |
| 2020/0038494 A1 | 2/2020 | Rebbeor et al. |

FOREIGN PATENT DOCUMENTS

| | | |
|---|---|---|
| CN | 102655876 A | 9/2012 |
| CN | 105254702 A | 1/2016 |
| EP | 2214699 B1 | 11/2016 |
| EP | 3130384 A1 | 2/2017 |
| JP | 2004-519447 A | 7/2004 |
| JP | 2009-167190 A | 7/2009 |
| JP | 2010-174036 A | 8/2010 |
| JP | 2015-221835 A | 12/2015 |
| RU | 2004118259 A | 11/2005 |
| WO | WO 2002/051390 A2 | 7/2002 |
| WO | WO 2004/060920 A1 | 7/2004 |
| WO | WO 2005/027821 A2 | 3/2005 |
| WO | WO 2005/048985 | 6/2005 |
| WO | WO 2011/056793 A2 | 5/2011 |
| WO | WO 2015/195453 | 12/2015 |
| WO | WO 2018/116300 A1 | 6/2018 |

OTHER PUBLICATIONS

Arunkumar et al., Investigation of single-pass tangential flow filtration (SPTFF) as an inline concentration step for cell culture harvest, Journal of Membrane Science, vol. 524, pp. 20-32, 2017.
Ayturk E. Understanding Single-Pass Tangential flow filtration and the new era bioprocessibg/BiopharmaAsia, 2016/cm, cited in the Office Action received in the counterpart Patent application in Russia.
Brantly M. et al/ intravenous Alpha-1 Antitrypsin Therapy for Alpha-1 Antitrypsin Deficiency: the Current State of the Evidence/ Chronic Obstructive Pulmonary Diseases: Journal of the COPD Foundation, 2019, vol. 6/cm, c. 109.
Casey, C., et al., Protein Concentration with Single-Pass Tangential Flow Filtration (SPTFF), Journal of Membrane Science 384(1):82-88, Sep. 3, 2011.
European Search Report in corresponding European Patent Application No. 19188500 dated Dec. 20, 2019, 6 pages.

(Continued)

*Primary Examiner* — Robert A Wax
*Assistant Examiner* — Quanglong N Truong
(74) *Attorney, Agent, or Firm* — Knobbe, Martens, Olson & Bear LLP (57) ABSTRACT

Compositions include highly concentrated Alpha-1 Proteinase Inhibitor (A1PI) in a concentration greater than or equal to 100 mg/ml. Pharmaceutical compositions can be prepared from these compositions. The pharmaceutical compositions can be suitable for subcutaneous administration. The highly concentrated A1PI solutions can be obtained by single-pass tangential flow filtration (SPTFF).

17 Claims, 5 Drawing Sheets

(56) References Cited

OTHER PUBLICATIONS

Kumar et al., Purification of A 1PI from Human Plasma—An Improved Process to achieve Therapeutic Grade Purity, Chromatography Separation Techniques, vol. 6, No. 4, 9 pages, 2015.

Nguyen Tran Thi Dat, "Synthesis of timed-release polymer nanoparticles", Australian Institute for Bioengineering and Nanotechnology, University of Queensland—188 pages (2014).

Patel et al. Alpha-1-Antitrypsin Deficiency Liver Disease / Clin Liver Dis, 2018, vol. 22, N4, pp. 643-655.

Payne et al., "Second Virial Coefficient Determination of a Therapeutic Peptide by Self-Interaction Chromatography", Biopolymers (Peptide Science), vol. 84, No. 5 ( Jun. 9, 2006).

Ч РАГ ЕВА И .М. Технология ферментных препаратов, 1987, 2-е изд/см . c.111. (Translation of relevant parts provided).

Search Report dated Sep. 29, 2020; received in Chilean Patent Application No. 2019-02131.

Second Office Action issued Nov. 30, 2022; in CN 2019106554846; which is related to the present application (English translation provided).

Office Action for RU 019122311/10(043627); which is related to the present application (English translation provided).

Search Report for RU 019122311/10(043627), which is related to the present application.

COMPOSITION COMPRISING HIGHLY-CONCENTRATED ALPHA1 PROTEINASE INHIBITOR AND METHOD FOR OBTAINING THEREOF

PRIORITY AND CROSS REFERENCE TO THE RELATED APPLICATIONS

This application is a continuation of the U.S. application Ser. No. 17/448,509, filed on Sep. 22, 2021, which is a continuation of U.S. application Ser. No. 16/529,686, filed on Aug. 1, 2019, which claims priority to U.S. Provisional Application No. 62/713,673, filed on Aug. 2, 2018. Any and all applications for which a foreign or a domestic priority is claimed is/are identified in the Application Data Sheet filed herewith and is/are hereby incorporated by reference in their entireties under 37 C.F.R. § 1.57.

BACKGROUND

Field

The present disclosure is related to the field of pharmaceutical products. Certain embodiments herein relate to compositions comprising highly-concentrated Alpha-1 Proteinase Inhibitor (A1PI), which can be used for many therapeutic indications, and methods for obtaining the compositions.

Description of the Related Art

Alpha-1-Proteinase inhibitor (A1PI), also known as Alpha-1-Antitrypsin (AAT) or $\alpha_1$-Antitrypsin, is a proteinase inhibitor that acts on a variety of cellular proteases. A1PI plays a major role in tissue homeostasis through the inhibition of neutrophil elastase action, and through other mechanisms.

Congenital deficiencies of A1PI allow uncontrolled activity of neutrophil elastase and the subsequent degradation of elastin, an essential protein that confers elasticity to tissues, particularly the lungs. The absence of elastin may result in respiratory complications such as pulmonary emphysema and hepatic cirrhosis.

Chronic intravenous (IV) administration of A1PI to treat AAT deficiency is burdensome, requires professional assistance (administered in the patient's home or in clinics, hospitals, etc), and can cause immediate hypersensitive reactions. To overcome said problems, a new concentration process and a new formulation have been developed by the inventors for a novel product which comprises highly concentrated A1PI. The concentrated formulation detailed in the invention enables a broader spectrum of parenteral administration, which may include intravenous, subcutaneous, aerosol, and intradermal administration. This product could satisfy the long-standing unmet need to make dosing easier to administer by patients at home, without a supporting healthcare professional, thus reducing treatment costs, and is suitable for chronic treatment.

The inventors of the present invention are not aware of any prior art method for obtaining A1PI with a concentration higher than 100 mg/ml. Attempts to increase the concentration of A1PI using conventional flat cassette tangential flow filtration (TFF) results in generation of unacceptable high level of aggregates even using small amount of buffer salts. The present inventors have surprisingly found that using a modified tangential flow ultrafiltration method that used the same membrane type and molecular weight cut-off (MWCO) as the conventional ultrafiltration/diafiltration (UFDF) step, but operated at reduced flow rates, higher transmembrane pressure (TMP), and larger membrane area to increase flow-path length, could concentrate A1PI to at least 10% (w/v, 100 mg/ml) in a single-pass tangential flow filtration (SPTFF) after it had been diafiltered against water to remove all process salts. The present inventors have surprisingly found that, using a further step of SPTFF against water for injection (WFI), it is possible to obtain a concentration of A1PI of at least 100 mg/ml, and said solution can be subsequent formulated with uncharged excipients to achieve isotonic conditions. This enabled formulation of a concentrated A1PI with uncharged excipients to adjust osmolality, while addressing the previous poor stability performance with charged excipients.

SUMMARY

An embodiment of the present disclosure provides a composition comprising Alpha-1 Proteinase Inhibitor (A1PI) in an aqueous solution, wherein the concentration of A1PI is greater than or equal to 100 mg/ml, preferably is greater than or equal to 150 mg/ml, more preferably is greater than or equal to 200 mg/ml.

In some preferred embodiments, the composition comprising A1PI further comprises one or more uncharged excipients. The term "uncharged excipients" mean that no net charge of one or greater is present at near neutral pH with said excipients.

In some preferred embodiments, the one or more uncharged excipients are at a concentration necessary to achieve isotonicity, i.e., between 220 and 410 mOsm/kg $H_2O$, preferably about 300 mOsm/kg $H_2O$.

In some preferred embodiments, the one or more uncharged excipients are selected from the list consisting of amino acids, sugars, and polyols, including sorbitol, serine, trehalose, alanine, sucrose, and mannitol and combinations thereof. More preferable, the one or more uncharged excipients are alanine, sorbitol or trehalose and combinations thereof.

In some preferred embodiments, said uncharged excipient(s) are in the composition at a concentration of approximately 120 mM, to achieve acceptable osmolality.

In some embodiments, the pharmaceutical composition can be administered to a patient in need thereof.

Another embodiment of the present disclosure provides a pharmaceutical composition comprising the above-mentioned composition and a pharmaceutically acceptable carrier.

In some embodiments, the pharmaceutical composition is formulated for intravenous, subcutaneous, aerosol, or intradermal administration, preferably for subcutaneous administration.

In some embodiments, the pharmaceutical composition is encapsulated in nanoparticles or it comprises a time-release polymer.

Another embodiment of the present disclosure provides a method for preparing the above-mentioned composition, comprising preparing a solution of A1PI by concentrating an initial solution of A1PI by SPTFF.

In some embodiments, a method for preparing a solution of A1PI by SPTFF wherein the final concentration of A1PI is at least 100 mg/ml, preferably at least 150 mg/ml, more preferably at least 200 mg/ml.

In some embodiments, a method for preparing a solution of A1PI by SPTFF is carried out against water for injection (WFI).

In some embodiments, a method for preparing a concentrated solution of A1PI comprises after the SPTFF step a formulation with one or more uncharged excipients selected from the list consisting of sorbitol, serine, trehalose, alanine, sucrose, and mannitol, and combinations thereof. More preferable, the one or more uncharged excipients are alanine, sorbitol or trehalose and combinations thereof.

pH is controlled to near neutral (around 6.6 to 7.4) without the use of buffers, but through adjustment upon addition of formulation excipient(s), and remains stable throughout storage.

DETAILED DESCRIPTION

Currently, A1PI solutions are commercially available (Prolastin-C, Grifols; Glassia, Shire; Zemaira, CSL; Aralast, Baxter) to treat human congenital deficiency of the protein (Alpha-1 Antitrypsin Deficiency, AATD). One limitation that all these products have in common is that they contain A1PI at relatively low concentrations (about 20 to 50 mg/ml). For this reason, their only suitable route of administration as a therapeutic has been weekly intravenous injection.

Chronic intravenous administration of A1PI to treat AATD is burdensome, requires professional assistance, and can cause immediate hypersensitive reactions. Therefore, there is a longstanding unmet need to make dosing easier to administer by patients at home without an assisting healthcare professional, which would considerably reduce treatment costs and would make it suitable for chronic treatment. In order to enable a wider range of parenteral administration routes, the concentration of A1PI in the products should be increased. However, it is not possible to produce stable concentrated liquid A1PI based on the current methods of A1PI purification, with existing formulations.

Surprisingly, the inventors found that including an additional step of SPTFF at the end of purification allowed the production of highly-concentrated A1PI of at least 100 mg/ml, preferably at least 150 mg/ml, and most preferably 200 mg/ml. The novelty of this step of the process is that it had to be performed in the absence of buffers and salts, in the presence of WFI and formulated later by addition of one or more uncharged excipients selected from the list consisting of sorbitol, serine, trehalose, alanine, sucrose, and mannitol, and combinations thereof, more preferably alanine, sorbitol or trehalose and combinations thereof. Importantly, the resulting compositions are suitable for human administration since they comply with the values of osmolality, stability, and viscosity required by the regulatory agencies.

Compositions of A1PI

In some embodiments, the present disclosure provides a composition comprising A1PI. In some embodiments, the composition comprises A1PI in an aqueous solution. In some embodiments, the concentration of A1PI in the composition is at least 100 mg/ml. In some embodiments, the concentration of A1PI in the composition is 150 mg/ml. In some embodiments, the concentration of A1PI in the composition is ≥200 mg/ml. In some embodiments, the concentration of A1PI in the composition is about 100, 140, 180, 220, 260, 300, 340, 380, 420, 460, or 500 mg/ml, or within a range defined by any two of the aforementioned values.

Pharmaceutical Compositions of A1PI

In some embodiments, a pharmaceutical composition is provided. In some embodiments, the pharmaceutical composition comprises an A1PI solution. In some embodiments, the concentration of A1PI in the solution is at least 100 mg/ml.

In some embodiments, the concentration of A1PI in the solution is about 100 mg/ml to about 500 mg/ml. In some embodiments, the concentration of A1PI in the solution is about 100, 150, 200, 300, 400, or 500 mg/ml, or within a range defined by any two of the aforementioned values.

In some embodiments, the osmolality of the solution is about 220 mOsm/kg to about 410 mOsm/kg. In some embodiments, the osmolality of the solution is about 220, 240, 270, 300, 330, 360, 390 or 410 mOsm/kg, or within a range defined by any two of the aforementioned values.

In some preferred embodiments, the pharmaceutical composition further comprises one or more uncharged excipients selected from the group consisting of amino acids, sugars, and polyols, including sorbitol, serine, trehalose, alanine, sucrose, and mannitol, and combinations thereof, more preferably alanine, sorbitol or trehalose and combinations thereof.

pH is controlled to near neutral (around 6.6 to 7.4) without the use of buffers, but through adjustment upon addition of formulation excipient(s), and remains stable throughout storage.

In some preferred embodiments, the pharmaceutical composition comprises one or more uncharged excipients at a final concentration of about 120 mM to achieve acceptable osmolality.

One or more embodiments of the pharmaceutical composition provided herein can be administered to a patient in need thereof. In some embodiments, the pharmaceutical composition is administered intravenously, intradermally, subcutaneously, intramuscular, orally, or a combination thereof.

In some embodiments, other non-limiting routes of administrations are contemplated, for example, parenteral, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal.

In some embodiments, the pharmaceutical compositions provided herein comprise active ingredients, inactive ingredients, excipients, and/or pharmaceutically acceptable carriers. A wide variety of pharmaceutically acceptable carriers are available and well-known in the art. The formulation of pharmaceutical compositions is determined in part by the particular composition being administered as well as by the particular method and/or route used to administer the composition.

Pharmaceutical compositions can comprise aqueous and non-aqueous, isotonic sterile injection solutions, which can comprise antioxidants, buffers, bacteriostats, and solutes that render the composition isotonic with the blood of the intended recipient, and aqueous and non-aqueous sterile suspensions that can include suspending agents, solubilizers, thickening agents, stabilizers, and preservatives.

In some embodiments, one or more embodiments of the pharmaceutical composition provided herein are used to treat one or more of respiratory complications such as pulmonary emphysema, chronic obstructive pulmonary disease, etc. In some embodiments, one or more embodiments of the pharmaceutical composition provided herein are used to treat hepatic complications such as hepatic cirrhosis. In some embodiments, one or more embodiments of the pharmaceutical composition provided herein are used to treat any disease or condition related to A1PI deficiency, or benefited by augmentation with A1PI.

Methods of Preparing Concentrated A1PI Solution

In some embodiments, a method of preparing a solution of A1PI is provided. In some embodiments, the method comprises concentrating a solution of A1PI in water or with uncharged excipients by conventional flat cassette tangential flow ultrafiltration (TFF). In some embodiments, the final concentration of A1PI in the concentrated solution is as much as 100 mg/ml.

In some embodiments, the method comprises concentrating a solution of A1PI in water or with uncharged excipients by SPTFF, where the final concentration of A1PI in the concentrated solution is about 150 mg/ml to about 500 mg/ml. In some embodiments, the final concentration of A1PI in the concentrated solution is about 150, 180, 200, 220, 260, 300, 340, 380, 420, 460, or 500 mg/ml, or within a range defined by any two of the aforementioned values.

In some preferred embodiments, the solution of A1PI in WFI is obtained by SPTFF.

In some embodiments, a method for preparing a concentrated solution of A1PI comprises, after the SPTFF step, a formulation with one or more uncharged excipients selected from the group consisting of amino acids, sugars, and polyols, including sorbitol, serine, trehalose, alanine, sucrose, and mannitol, and combinations thereof, more preferably alanine, sorbitol or trehalose and combinations thereof.

pH is controlled to near neutral (around 6.6 to 7.4) without the use of buffers, but through adjustment upon addition of formulation excipient(s), and remains stable throughout storage.

In some preferred embodiments, the concentration uncharged excipient in the composition is about 0.12 M, or sufficient to adjust osmolality to isotonicity.

Additional Embodiments

Thus, in some embodiments, alternate methods of administration are employed for such a concentrated A1PI formulation. For example, nano-encapsulation (i.e., encapsulation in nanoparticles) with time-release polymer for intradermal dosing. Such time release polymers for nano-encapsulation are well-known to those skilled in the art. For example, Tran Thi Dat Nguyen (2015), "Synthesis of timed-release polymer nanoparticles," of the Australian Institute for Bioengineering and Nanotechnology at the University of Queensland, available in the espace library of the University of Queensland under DOI 10.14264/uq1.2015.605 describes the use of nanoparticles self-assembled from random thermoresponsive copolymers, such as copolymers of PNIPAM and PDMAEA. The complete disclosure of this article is hereby incorporated by this reference thereto. Other methods are also applicable to achieve safe dosing of highly concentrated A1PI.

EXAMPLES

Comparative Example 1—High Concentration A1PI Process Flow According to the Prior Art Alpha-1 MP (U.S. Pat. No. 6,462,180 B1), Liquid Alpha (U.S. Pat. No. 9,616,126 B1), and Alpha-1 HC (US 20110237781 A1) processes make A1PI up to 50 mg/ml using a typical recirculating (TFF) UF step to concentrate, followed by a diafiltration (DF) step with water to remove buffer salts to prepare bulk for final formulation and adjustment to 50 mg/ml of protein. The formulation consists of a 20 mM sodium phosphate buffer to maintain pH, and either a salt (Alpha-1 MP and Alpha-1 HC; 100 mM or 150 mM NaCl, respectively) or amino acid (Liquid Alpha; 200 to 300 mM alanine) to adjust osmolality to isotonic conditions of 220-410 mOsm/kg. Likewise, other A1PI formulations are similarly prepared (Table 1).

TABLE 1

A side by side comparison of several A1PI preparations, with concentration and formulations.

| Grifols; 2002 U.S. Pat. No. 6,462,180 Prolastin-C | ARC; 2000 U.S. Pat. No. 6,093,804 | Kamada; 2011 U.S. Pat. No. 7,879,800 Glassia | CSL; 2012 U.S. Pat. No. 8,124,736 Zemaira | Alpha Therapeutics 1999 U.S. Pat. No. 5,981,715 Aralast |
|---|---|---|---|---|
| 50 mg/ml; 0.02M NaP, 0.1M NaCl, pH 6.6-7.4 | 10-20 mg/ml; 0.02M NaP, 0.1M NaCl, pH 6.8-7.0 | 20-40 mg/ml; 0.02M NaP, 0.1M NaCl, pH 6.5-7.5 | 50 mg/ml; 0.02M NaP, 0.045M NaCl, 3% mannitol, pH 6.6-7.4 | 20 mg/ml; 0.02M NaP, 0.1M NaCl, pH 8.0 |

Figure 1:
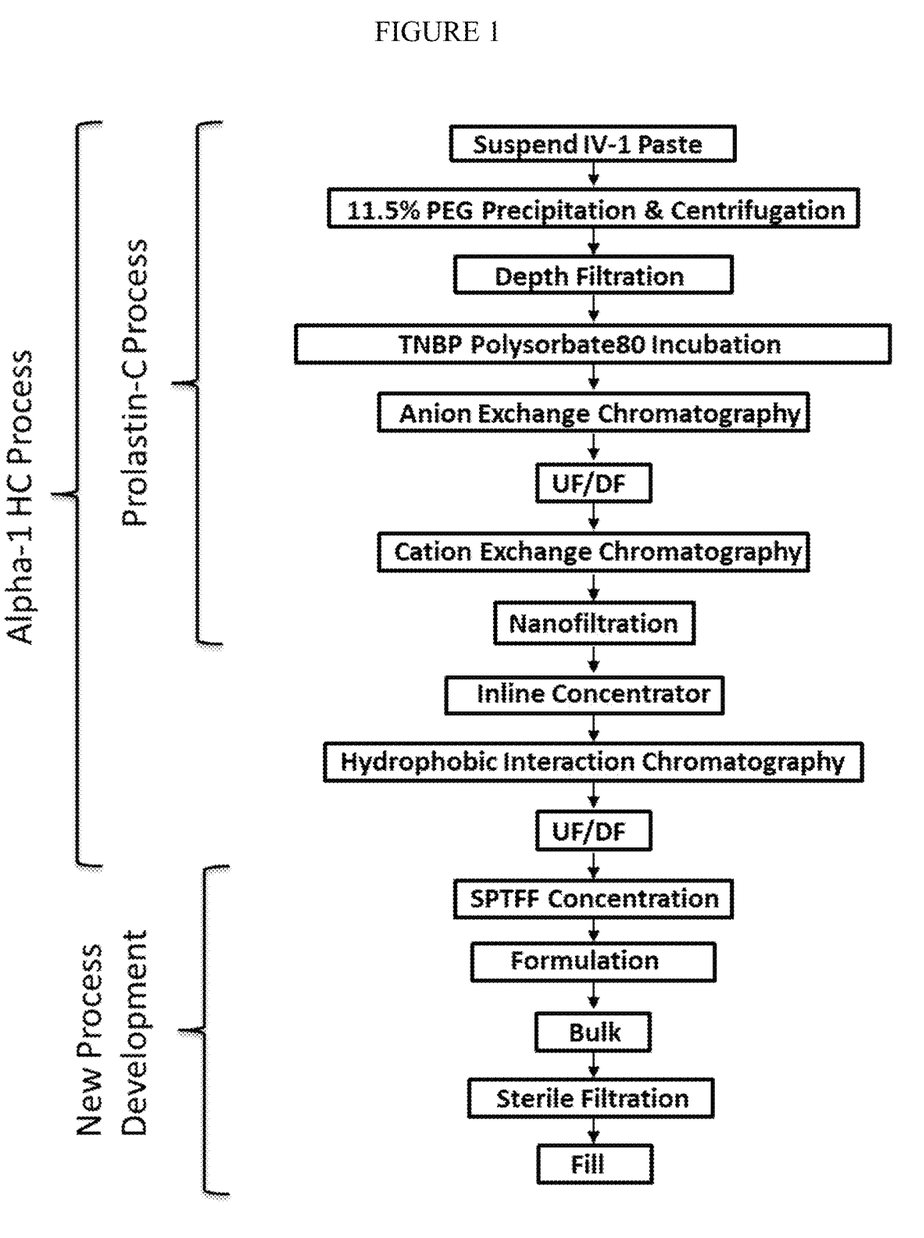
FIG. 1 shows an embodiment of a method in which a SPTFF step and a formulation are added to a prior art process.

As explained above, the process of the present invention incorporates two additional steps to the above process: SPTFF concentration and formulation, as shown in FIG. 1.

Figure 2:
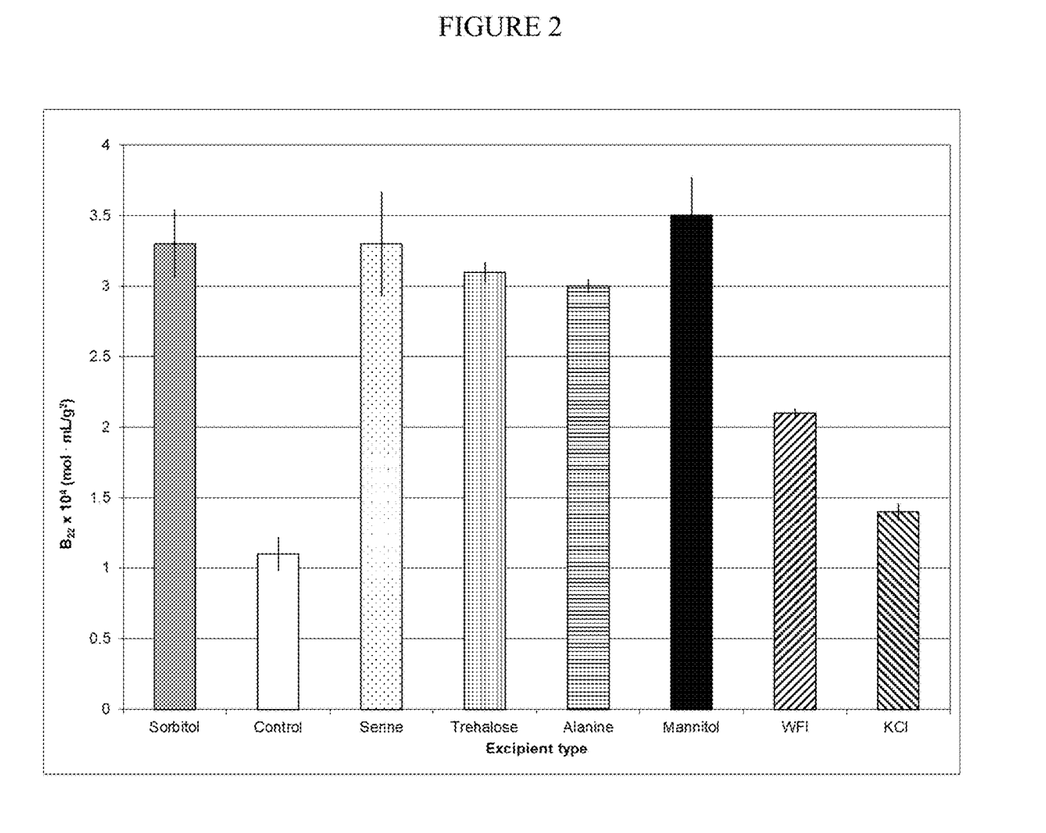
FIG. 2 shows $B_{22}$ vs. excipient type from self-interacting chromatography (SIC) experiments.

Example 2—Evaluation of $B_{22}$ Value as a Indicator of Aggregation in the Uncharged Excipients A1PI Solutions Obtained with the Process of the Present Invention The process of the present invention involves a SPTFF concentration with WFI and a formulation with uncharged excipients. Several of the uncharged excipients at 0.12 M concentrations, pH 7.0, as well as low pH or high salt formulation controls, were used to make 20% A1PI solutions and applied to Self-interacting chromatography (SIC) columns produced by conjugating A1PI to a Toyopearl AF-formyl-650 M (Tosoh Biosciences) resin, and the retention time recorded. The retention time of the protein was converted to the osmotic second virial coefficient ($B_{22}$), which is a measure of protein-protein interactions. FIG. 2 presents a plot of $B_{22}$ vs excipient type. The higher the $B_{22}$ value the greater the protein-protein repulsion (preferred to minimize aggregation) (Payne et al., "Second Virial Coefficient Determination of a Therapeutic Peptide by Self-Interaction Chromatography" Biopolymers (Peptide Science), Vol. 84, 527-533 (2006)). The lowest $B_{22}$ values were predictably observed for the low pH negative control (0.12 M KCl, pH 6.0) and the formulation control (20 mM sodium phosphate, 75 mM NaCl, pH 7.0), conditions which were known to be the least favorable (highest protein-protein interaction) for A1PI. Sorbitol, serine, trehalose, alanine and mannitol all had higher $B_{22}$ values, indicating more protein repulsion, with mannitol having the highest $B_{22}$ value. WFI solutions, which relied on intrinsic charge repulsion at pH 7.0, had intermediate $B_{22}$ values. The uncharged excipients were at 0.12 M and pH 7.0.

Example 3—Evaluation of A1PI Aggregation in the Uncharged Excipients

Figure 3:
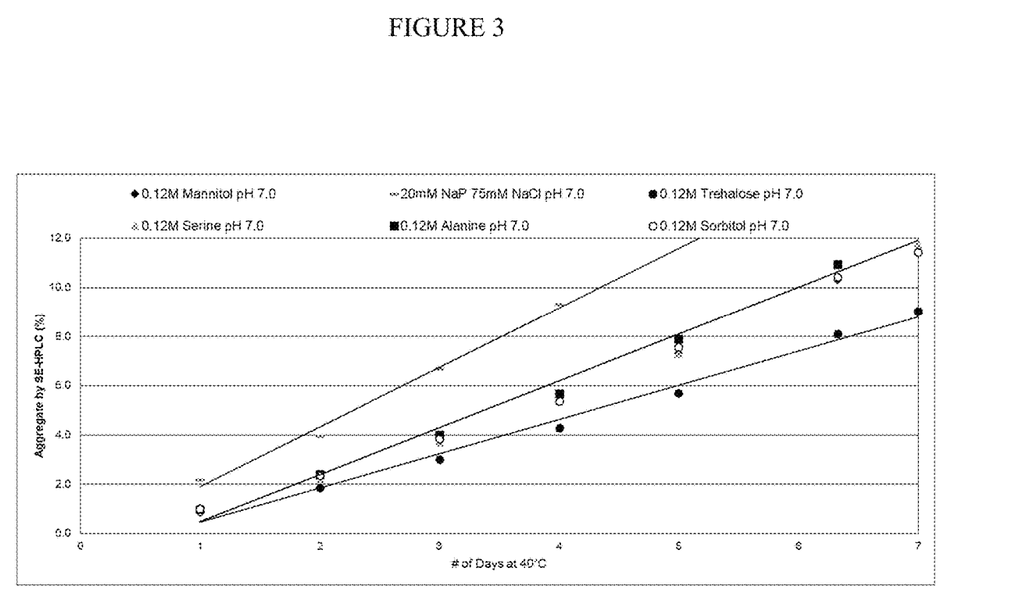
FIG. 3 shows the aggregate percentage vs. days for A1PI 20% formulations at 40° C.

Thermal kinetics studies of 20% A1PI formulations at 40° C. measured accelerated aggregation by SE-HPLC over time. A1PI 20% solutions of various 0.12 M excipient formulations (mannitol, alanine, serine, sorbitol, and trehalose) at pH 7.0, along with the control formulation (16 mM sodium phosphate, 60 mM NaCl, pH 7.0), were incubated at 40° C. for 7 days and analyzed by SE-HPLC (FIG. 3). These data grouped in three categories, with the control formulation having the highest aggregation rate, as expected, while mannitol, alanine, serine and sorbitol had an intermediate aggregation rate, and trehalose had a significantly lower aggregation rate than the others. In conclusion, the results show that less aggregation occurred in the presence of uncharged excipients, compared with the control.

Example 4—Evaluation of A1PI Stability in the Presence of Uncharged Excipients

Figure 4:
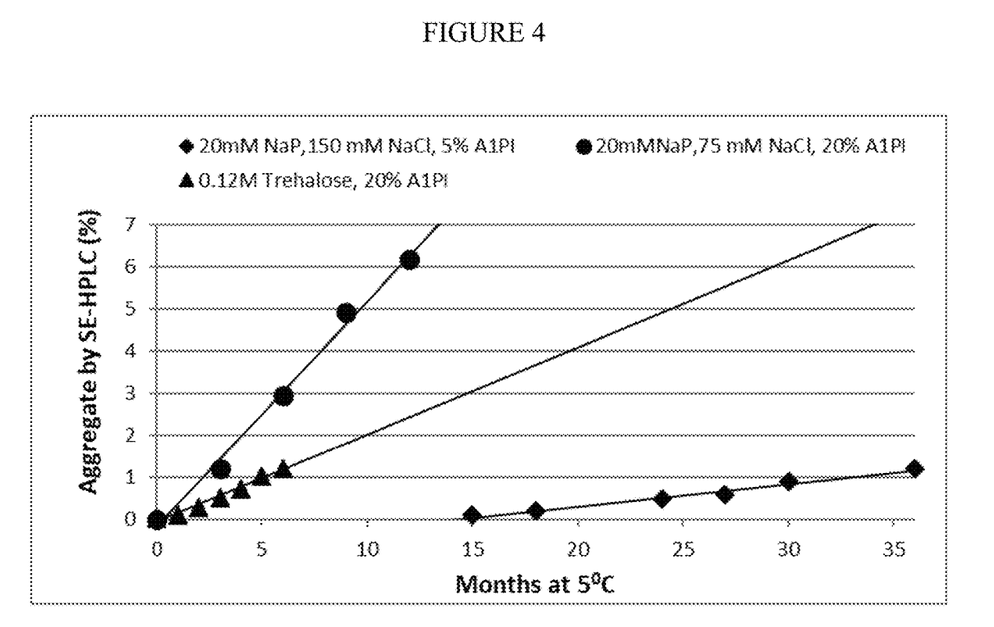
FIG. 4 shows the aggregate percentage measured by size exclusion high-performance liquid chromatography (SE-HPLC) in the liquid formulations of A1PI stored in vials at 5° C.

On the other hand, the aggregation was measured by SE-HPLC over time and at different A1PI concentrations in the presence of charged and uncharged excipients. A1PI solutions of FIG. 4 show the aggregation percentage in vials stored at 5° C. A1PI at ~50 mg/mL (diamonds) and A1PI at ~200 mg/mL (circles) with salt to control osmolality, and A1PI at ~200 mg/mL formulated in only 0.12 M trehalose (triangles) show different rates of aggregation. Similar to what Bauer (U.S. Pat. No. 7,879,800) showed in Table 12, the 20% A1PI formulated in 20 mM sodium phosphate 75 mM sodium chloride, pH 7.0 had a very high rate of aggregation, compared to A1PI in similar excipients at 5%. However, the 20% A1PI formulated with only 120 mM trehalose, pH 7.0 showed much less aggregation under identical storage conditions.

Example 5—Daily or Weekly Dosing of A1PI for a 70 kg/100 kg Patient with Either Subcutaneous (SC) or Intravenous (IV) Administration It is understood that subcutaneous dosing is volume constrained, with single-site injections often limited to about 25 mL. Therefore, a higher concentration of A1PI is needed to achieve dosing to prescribed amounts. Current dosing to 60 mg/kg can be achieved, with a 1.2 absorption coefficient (EP 2,214,699 B1), with weekly dosing of 15% A1PI at 2 sites or with 20% A1PI at a single site for the average patient (Table 2).

TABLE 2

Daily or weekly dosing of Alpha-1 HC for a 70 kg/100 kg patient with either subcutaneous (SC) or intravenous (IV) administration would be most feasible with concentrations at or above 150 mg/ml.

| A1PI Concentration (mg/ml) | Daily SC Dosing (ml)* 70 kg patient/ 100 kg patient | Weekly SC Dosing (ml)* 70 kg patient/ 100 kg patient | Weekly IV Dosing (ml)* 70 kg patient/ 100 kg patient |
|---|---|---|---|
| 50 | 14.4/20.6 | 100.8/144 | 84/120 |
| 100 | 7.2/10.3 | 50.4/72 | 42/60 |
| 150 | 4.8/6.9 | 33.6/48 | 28/40 |
| 200 | 3.6/5.1 | 25.2/36 | 21/30 |

*Assuming a 120% multiplier for SC absorption adjustment.

Example 6—Highly Concentrated A1PI by SPTFF

A method to achieve compositions comprising highly concentrated A1PI, which could be used for many therapeutic indications, includes the application of SPTFF. The SPTFF step would follow the diafiltration step in WFI (FIG. 1). The SPTFF can concentrate the A1PI to higher concentrations in WFI than can be achieved with conventional TFF (above 100 mg/mL), with only a single pass through the UF membrane assembly at lower pumps speeds, reducing exposure to heat and stress associated with TFF continued pump circulations. The increased flow path length combined with a reduced flow rate at higher transmembrane pressure enables higher concentrations of A1PI to be achieved [>25% (w/v)] by SPTFF in the presence of WFI alone. Finally, the concentrated A1PI solution is precisely diluted to a target concentration [at least 10% (w/v)] with a concentrated excipient solution at pH adjusted to 7.0 to accomplish osmolality adjustment with either amino acids, sugars, or polyols (represented in Table 3 by alanine, trehalose, and sorbitol, respectively). This process enables high A1PI concentrations to be achieved, while stable formulations of the liquid drug product result without the use of buffers, salts, or surfactants.

TABLE 3

Total protein concentration, specific activity, SE-HPLC, osmolality, and viscosity data for the SPTFF experiments with various excipients.

| Bulk Sample Description | Total Protein (mg/mL) | Specific Activity (potency/ total protein) | SE-HPLC | | | Osmolality (mOsm/kg) | Viscosity (cP) |
|---|---|---|---|---|---|---|---|
| | | | Aggregate | Oligomer | Monomer | | |
| UFDF in WFI | 109 | 1.1 | <0.1 | 3.70 | 96.27 | 51 | 2.9 |
| SPTFF in WFI | 261 | 1.1 | <0.1 | 3.96 | 96.05 | 249 | 52.7 |
| 0.12 M Alanine, pH 7.0 | 202.1 | 1.0 | 0.05 | 3.96 | 95.29 | 292 | 11.2 |

TABLE 3-continued

Total protein concentration, specific activity, SE-HPLC, osmolality, and viscosity data for the SPTFF experiments with various excipients.

| Bulk Sample Description | Total Protein (mg/mL) | Specific Activity (potency/total protein) | SE-HPLC | | | Osmolality (mOsm/kg) | Viscosity (cP) |
| --- | --- | --- | --- | --- | --- | --- | --- |
| | | | Aggregate | Oligomer | Monomer | | |
| 0.12 M Trehalose, pH 7.0 | 191 | 1.2 | 0.04 | 3.91 | 94.83 | 323 | 13.4 |
| 0.12 M Sorbitol, pH 7.0 | 194.2 | 1.1 | 0.06 | 4.03 | 95.22 | 307 | 12.7 |

Example 7—pH Range Measured by Zeta Potential

Figure 5:
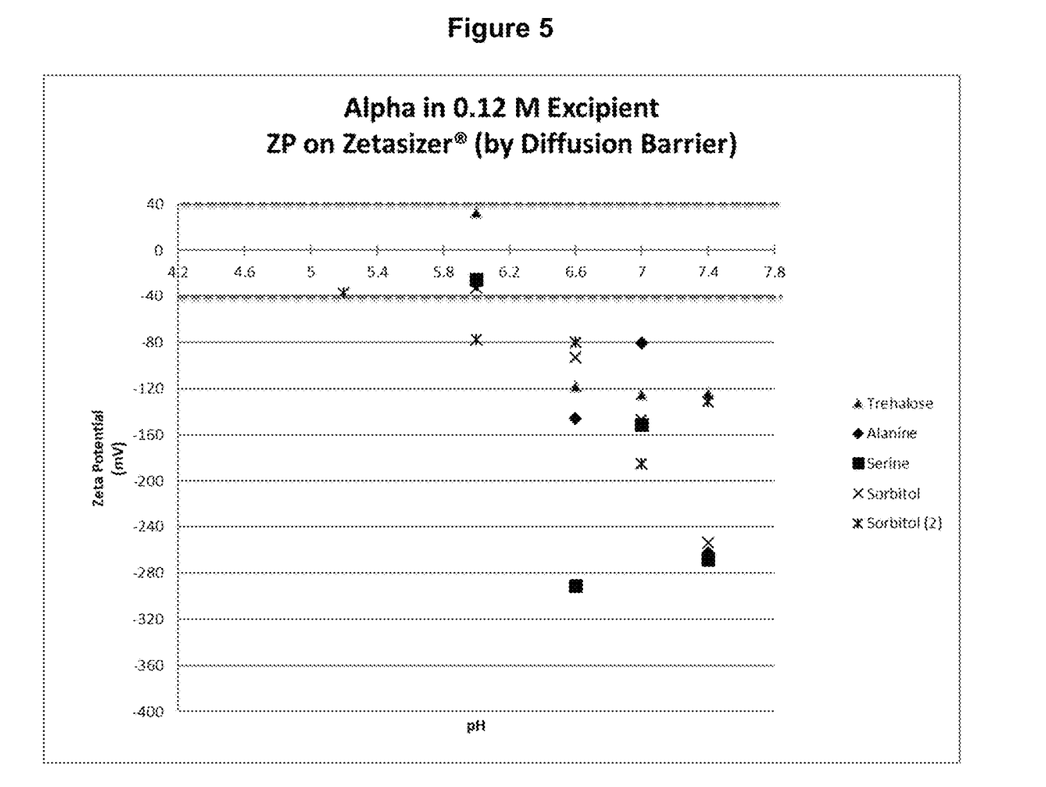
FIG. 5 shows the Zeta Potential vs. pH of different formulations of A1PI at 0.12 M.

Zeta Potential measurements for A1PI solutions with 0.12 M excipient concentrations were evaluated across various pHs using a Zetasizer. Higher magnitude of zeta potential (≥40 mV or ≤−40 mV) represents better colloidal stability, as molecules that are sufficiently charged tend to be electrostatically repulsive and are less likely to form aggregates in solution. All A1PI formulations tested (FIG. 5) showed colloidal stability within the pH range of 6.6 to 7.4, based on measured ZP values below −40 mV. In each formulation the zeta potential trended towards 0 as the pH approached the A1PI isoelectric point (between 4.0 and 5.0).

Definitions

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein.

In this application, the use of the singular includes the plural unless specifically stated otherwise. Also, the use of "comprise", "comprises", "comprising", "contain", "contains", "containing", "include", "includes", and "including" are not intended to be limiting.

As used in this specification and claims, the singular forms "a," "an" and "the" include plural references unless the content clearly dictates otherwise.

As used herein, "about" means a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

Although this disclosure is in the context of certain embodiments and examples, those skilled in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of skill in the art based upon this disclosure.

It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above.

It should be understood, however, that this detailed description, while indicating preferred embodiments of the disclosure, is given by way of illustration only, since various changes and modifications within the spirit and scope of the disclosure will become apparent to those skilled in the art.

The terminology used in the description presented herein is not intended to be interpreted in any limited or restrictive manner. Rather, the terminology is simply being utilized in conjunction with a detailed description of embodiments of the systems, methods and related components. Furthermore, embodiments may comprise several novel features, no single one of which is solely responsible for its desirable attributes or is believed to be essential to practicing the embodiments herein described.

What is claimed is:

1. A composition comprising Alpha1-Proteinase Inhibitor (A1PI) in an aqueous solution and one or more uncharged excipients that maintain pH to around 6.6 to 7.4 without the use of buffers such that the composition is buffer-free, wherein the concentration of A1PI is greater than 100 mg/ml.

2. The composition of claim 1, wherein the concentration of A1PI is greater than or equal to 150 mg/ml.

3. The composition of claim 1, wherein the concentration of A1PI is greater than or equal to 200 mg/ml.

4. The composition of claim 1, wherein said one or more uncharged excipient is at a concentration to achieve an osmolality between 220 and 410 mOsm/kg $H_2O$.

5. The composition of claim 4, wherein said one or more uncharged excipient is at a concentration to achieve an osmolality of about 300 mOsm/kg $H_2O$.

6. The composition of claim 1, wherein the one or more uncharged excipient is selected from the group consisting of sorbitol, serine, trehalose, alanine, sucrose, and mannitol, and combinations thereof.

7. The composition of claim 6, wherein the one or more uncharged excipient is selected from the group consisting of sorbitol, trehalose, alanine, and combinations thereof.

8. A pharmaceutical composition comprising the composition according to claim 1 and a pharmaceutically acceptable carrier.

9. The pharmaceutical composition of claim 8, wherein the pharmaceutical composition is formulated for intravenous, subcutaneous, aerosol, or intradermal administration.

10. The pharmaceutical composition of claim 9, wherein the pharmaceutical composition is formulated for subcutaneous administration.

11. The pharmaceutical composition of claim 8, wherein the pharmaceutical composition is encapsulated in nanoparticles.

12. The pharmaceutical composition of claim 8, wherein the pharmaceutical composition comprises a time-release polymer.

13. A method for preparing a composition according to claim 1, comprising a step of preparing a solution of A1PI by concentrating an initial solution of A1PI by single-pass tangential flow filtration (SPTFF).

14. A method for preparing a composition according to claim 13, wherein said step of SPTFF is carried out against water for injection (WFI).

15. A method for preparing a composition according to claim 13, wherein after the SPTFF step the solution of A1PI is formulated with one or more uncharged excipients selected from the group consisting of sorbitol, serine, trehalose, alanine, sucrose, and mannitol, and combinations thereof.

16. A method for preparing a composition according to claim 15, wherein after the SPTFF step the solution of A1PI is formulated with sorbitol, trehalose, alanine, or a combination thereof.

17. The composition of claim 3, wherein the concentration of A1PI is greater than 200 mg/ml.

* * * * *

UNITED STATES PATENT AND TRADEMARK OFFICE
CERTIFICATE OF CORRECTION

PATENT NO. : 12,144,849 B2
APPLICATION NO. : 18/316850
DATED : November 19, 2024
INVENTOR(S) : James Rebbeor et al.

Page 1 of 1

It is certified that error appears in the above-identified patent and that said Letters Patent is hereby corrected as shown below:

On the Title Page

Column 2, Line 5, item (56), other pubs. delete "era bioprocessibg/" and insert -- era bioprocessing/ --.

Column 1, Page 2, Line 1, item (56) delete "of A 1PI from" and insert -- of A1PI from --.

In the Specification

Column 2, Line no. 2, delete "(UFDF) step," and insert -- (UF/DF) step, --.

Column 4, Line no. 53, delete "intrarticular, intrabronchial," and insert -- intraarticular, intrabronchial, --.

Column 4, Line no. 54, delete "intracelebellar, intracerebroventricular," and insert -- intracerebellar, intracerebroventricular, --.

Column 4, Lines no. 56 and 57, delete "intrapelvic, intrapericardiac," and insert -- intrapelvic, intrapericardial, --.

Column 7-8, TABLE 3, Line 8 (approx.), delete "UFDF in" and insert -- UF/DF in --.

Signed and Sealed this
Fourth Day of March, 2025

Coke Morgan Stewart
*Acting Director of the United States Patent and Trademark Office*